US00PP36300P2

(12) United States Plant Patent
Sills et al.

(10) Patent No.: US PP36,300 P2
(45) Date of Patent: Dec. 10, 2024

(54) BLACKBERRY PLANT NAMED 'DrisBlackThirtyThree'

(50) Latin Name: ***Rubus* L. subgenus *Rubus*.**
Varietal Denomination: DrisBlackThirtyThree

(71) Applicant: Driscoll's, Inc., Watsonville, CA (US)

(72) Inventors: Gavin R. Sills, Gilroy, CA (US); Yunwen Wang, Aptos, CA (US); Mark F. Crusha, Santa Cruz, CA (US); John Fangary, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 9 days.

(21) Appl. No.: 18/410,873

(22) Filed: Jan. 11, 2024

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./156, 203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear et al. |
| PP13,758 | P3 | 5/2003 | Fear et al. |
| PP13,759 | P3 | 5/2003 | Fear et al. |
| PP14,682 | P3 | 4/2004 | Fear et al. |
| PP14,765 | P2 | 5/2004 | Cook et al. |
| PP14,780 | P2 | 5/2004 | Cook et al. |
| PP15,058 | P2 | 8/2004 | Cook et al. |
| PP17,162 | P3 | 10/2006 | Moore et al. |
| PP17,983 | P2 | 9/2007 | Cabrera |
| PP22,002 | P2 | 7/2011 | Pabon et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Rodriguez et al. |
| PP24,701 | P3 | 7/2014 | Rodriguez et al. |
| PP24,878 | P2 | 9/2014 | Alcazar et al. |
| PP25,502 | P3 | 5/2015 | Pabon et al. |
| PP26,501 | P3 | 3/2016 | Pabon et al. |
| PP26,611 | P3 | 4/2016 | Pabon et al. |
| PP26,774 | P3 | 5/2016 | Pabon et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| PP31,110 | P2 | 11/2019 | Sills et al. |
| PP31,291 | P2 | 12/2019 | Sills et al. |
| PP31,825 | P2 | 6/2020 | Sills et al. |
| PP31,826 | P2 | 6/2020 | Sills et al. |
| PP32,268 | P2 | 10/2020 | Sills et al. |
| PP33,067 | P2 | 5/2021 | Sills et al. |
| PP33,068 | P2 | 5/2021 | Sills et al. |
| PP33,088 | P2 | 5/2021 | Sills et al. |
| PP34,069 | P2 | 3/2022 | Sills et al. |
| PP34,291 | P2 | 6/2022 | Sills et al. |
| PP34,320 | P2 | 6/2022 | Escobedo et al. |
| PP34,438 | P2 | 7/2022 | Sills et al. |
| PP34,481 | P2 | 8/2022 | Sills et al. |
| PP35,078 | P2 | 4/2023 | Sills et al. |
| PP35,233 | P2 | 6/2023 | Sills et al. |

OTHER PUBLICATIONS

Voss, Donald H. The Royal Horticultural Society Colour Chart 2001 Journal American Rhododendron Society, vol. 56, No. 1 2002 3 pages.

Williams, et al. DNA polymorphisms amplified by arbitrary primers are useful as genetic markers Nucleic Acids Research, vol. 18, No. 22 1990 pp. 6531-6535.

*Primary Examiner* — Karen M Redden
(74) *Attorney, Agent, or Firm* — Morrison & Foerster LLP

(57) ABSTRACT

A new and distinct variety of blackberry plant named 'DrisBlackThirtyThree', particularly selected for its yield potential, fruit size and flavor, shelf-life, spinelessness, and its moderate resistance to Fusarium wilt, is disclosed.

4 Drawing Sheets

Latin name: Botanical classification: *Rubus* L. subgenus *Rubus*.

Varietal denomination: The varietal denomination of the claimed variety of blackberry plant is 'DrisBlackThirtyThree'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed that are capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackThirty Three'.

Blackberry plant variety 'DrisBlackThirtyThree' was selected in Santa Cruz County, California in July of 2017 and originated from a controlled cross between the female parent blackberry plant 'DrisBlackEight' (U.S. Plant Pat. No. 26,501) and the male parent blackberry plant 'DrisBlackTwentyThree' (U.S. Plant Pat. No. 33,067). The original seedling of the new variety was first asexually propagated via root cuttings in Santa Cruz County, California in November of 2017.

'DrisBlackThirtyThree' was subsequently asexually propagated via root cuttings, and underwent testing in Santa Cruz County, California from 2017 to 2023 (six years). The present variety has been found to be stable and reproduce true to type through successive asexual propagations via root cuttings and tissue culture.

'DrisBlackThirtyThree' was selected for its yield potential, fruit size and flavor, shelf-life, spinelessness, and its moderate resistance to *Fusarium* wilt.

BRIEF DESCRIPTION OF THE DRAWINGS

This new blackberry plant is illustrated by the accompanying photographs. The colors shown are as true as can be reasonably obtained by conventional photographic procedures. The photographs are of plants that are three to five years old.

DETAILED BOTANICAL DESCRIPTION

Figure 1:
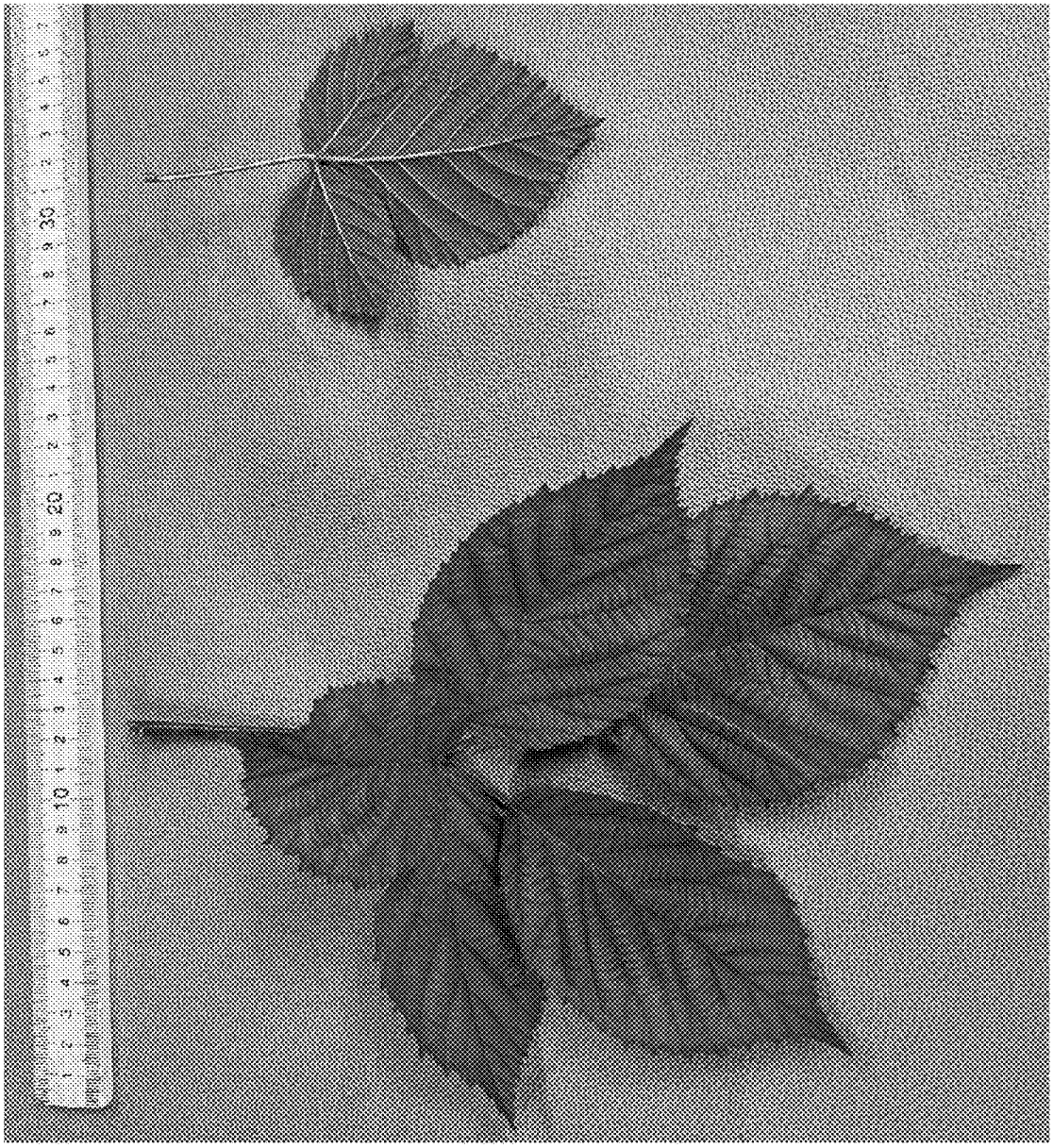
FIG. 1 illustrates the upper surface (left) and lower surface (right) of leaves of variety 'DrisBlackThirtyThree'.
Figure 2:
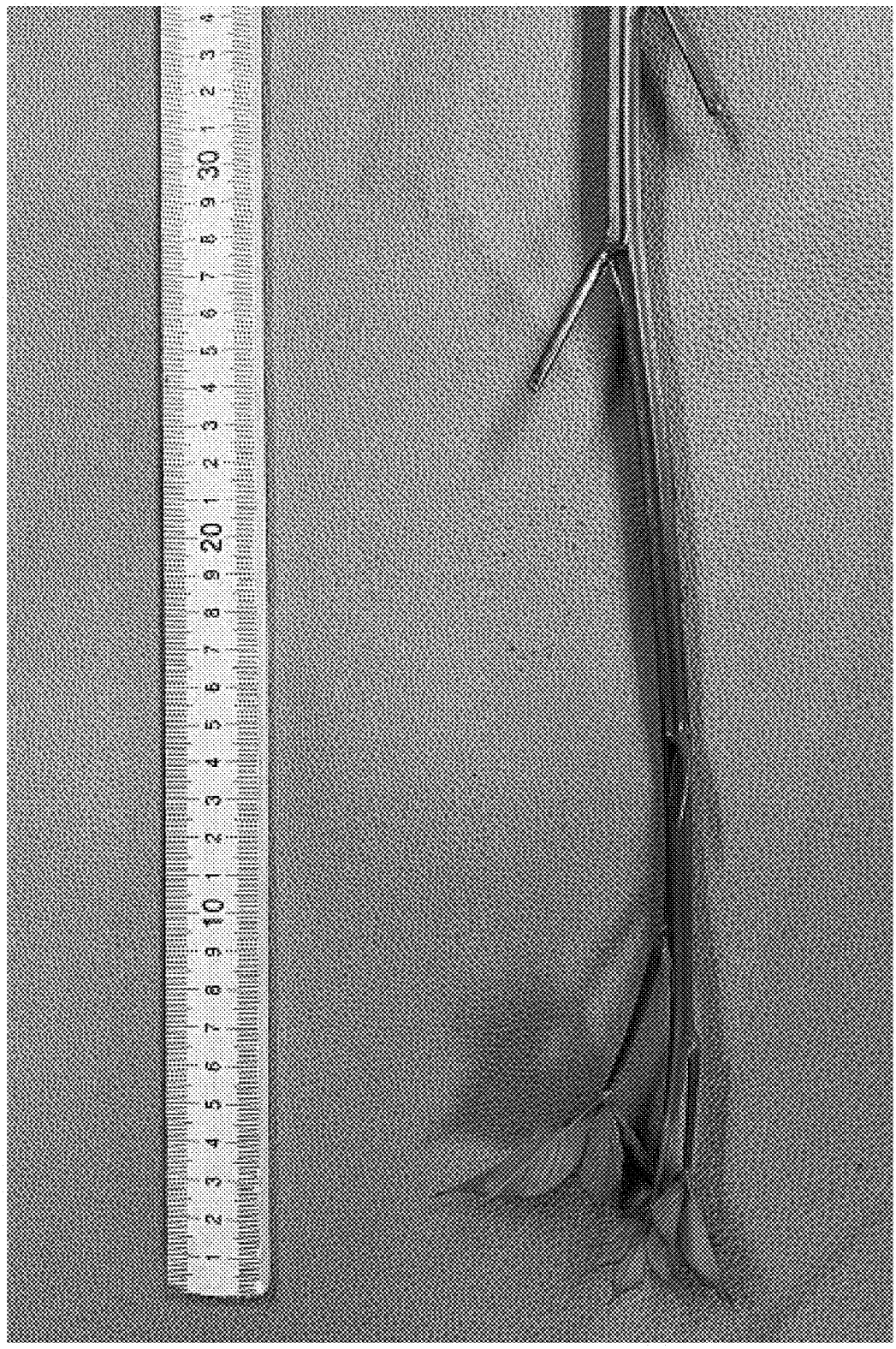
FIG. 2 illustrates a section of a cane of variety 'DrisBlackThirty Three'.
Figure 3:
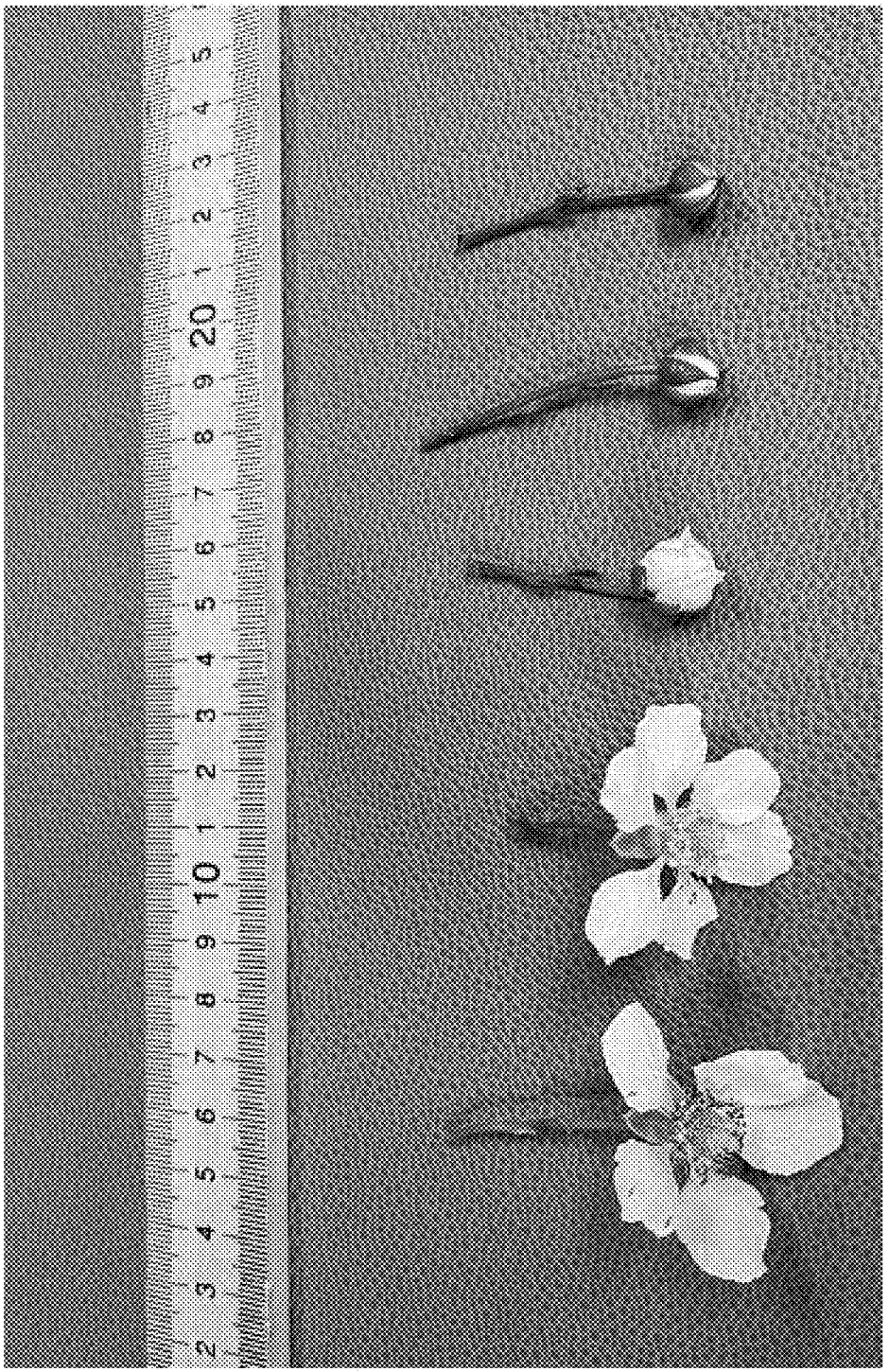
FIG. 3 illustrates flowers of variety 'DrisBlackThirtyThree' at various stages of development.
Figure 4:
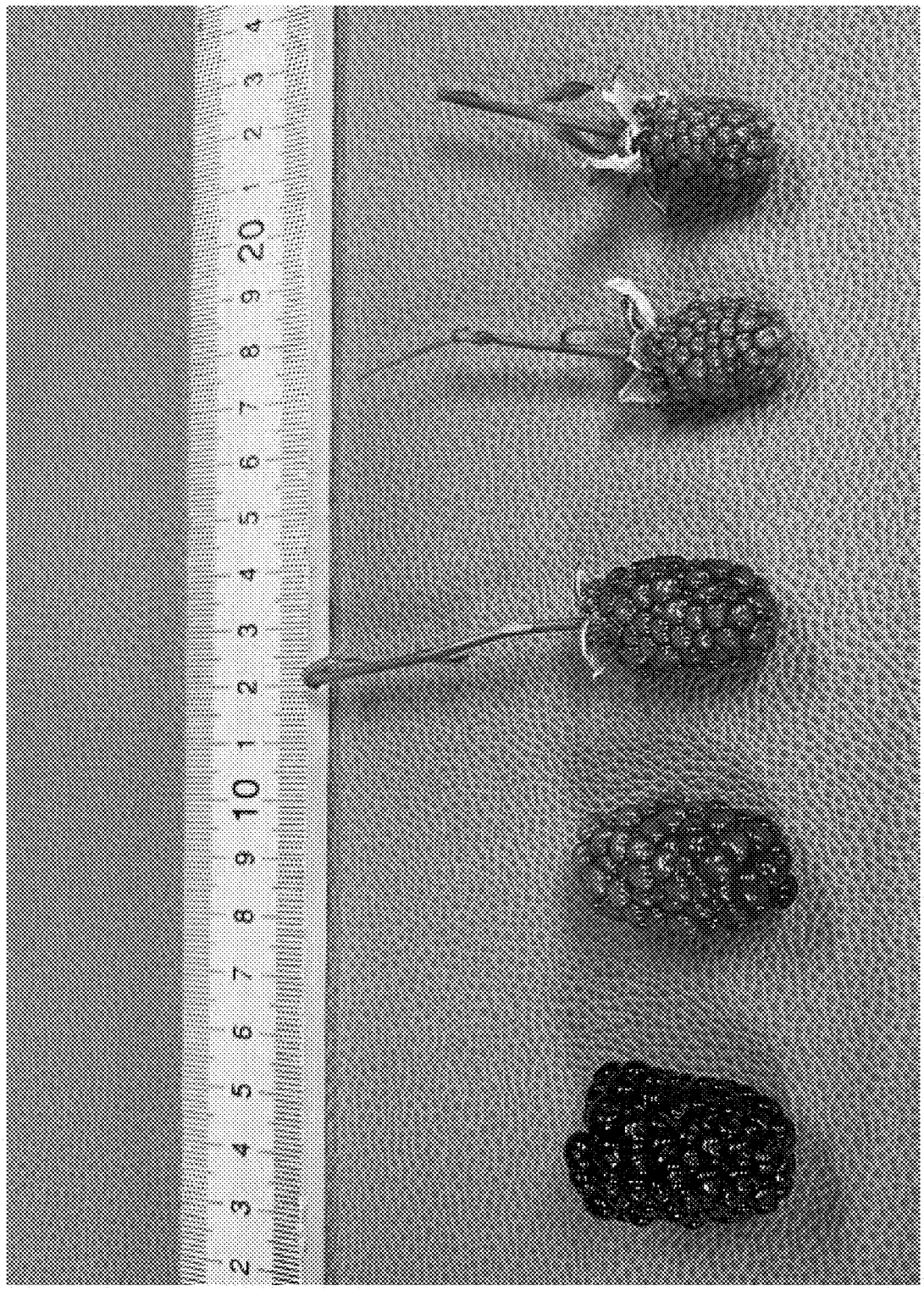
FIG. 4 illustrates fruits of variety 'DrisBlackThirtyThree' at various stages of development.

The following descriptions set forth the distinctive characteristics of 'DrisBlackThirtyThree'. The data that define these characteristics are based on observations taken in Santa Cruz County, California from 2017 to 2023. This description is in accordance with UPOV terminology. Color designations, color descriptions, and other phenotypical descriptions may deviate from the stated values and descriptions depending upon variation in environmental, seasonal, climatic and cultural conditions. 'DrisBlackThirtyThree' has not been observed under all possible environmental conditions. The botanical description of 'DrisBlackThirtyThree' was taken from plants that were three to five years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Family.*—Rosaceae.

*Botanical.*—*Rubus* L. subgenus *Rubus.*

*Common name.*—Blackberry.

*Variety name.*—'DrisBlackThirtyThree'.

Parentage:

*Female parent.*—'DrisBlackEight' (U.S. Plant Pat. No. 26,501).

*Male parent.*—'DrisBlackTwentyThree' (U.S. Plant Pat. No. 33,067).

Plant:

*Propagation.*—Root cuttings and tissue culture.

*Growth habit.*—Upright.

*Height.*—194.6 cm.

*Width.*—95.8 cm.

*Height/width ratio.*—2.03.

*Vigor.*—Medium.

*Self-fruitfulness.*—Self-fruitful.

Canes:

*Internodal distance.*—6.7 cm.

*New cane.*—Strength: Medium. Glaucosity (waxy bloom): Strong.

*Dormant cane.*—Anthocyanin coloration: Medium. Overall coloration: RHS 139D (Moderate yellow green). Predominant distribution of branches: Only on upper third. Cross-section: Angular to grooved. Spine: Presence of spines: Absent.

*Fruiting lateral.*—Fruiting lateral length ($4^{th}$ lateral from tip): 82.4 cm. Number of fruits per fruiting lateral: 21.2.

*Young shoots.*—Length: 106 cm. Diameter: 1 cm. Anthocyanin coloration (during rapid growth): Medium. Overall color: RHS 139D (Moderate yellow green). Number of glandular hairs: Absent or few. Time of young shoot emergence: Mid-March.

Leaves:

*Time of leaf bud burst.*—Late March to April.

*Leaf.*—Predominant number of leaflets: 3. Type: Palmate. Relative position of lateral leaflets: Overlapping. Arrangement: Whorled. Venation: Cross-venulate. Vein color: RHS 139D (Moderate yellow green). Color of upper side: RHS 139A (Dark yellowish green). Color of lower side: RHS 139C (Moderate yellow green). Profile in cross-section: Concave (margins rolled inwards). Glossiness of upper side: Medium.

*Leaflet.*—Type of incision of margin: Bi-serrate. Depth of margin incisions: Medium.

*Terminal leaflet.*—Length: 12.9 cm Width: 9.4 cm. Length/width ratio: 1.37. Shape: Oval. Base: Obtuse. Margin: Doubly serrate. Lobing: Absent. Shape in cross-section: U-shaped. Undulation of margin: Absent or very weak. Blistering between veins: Weak.

*Lateral leaflet* (*single leaflet in basal pair*).—Length: 9.5 cm. Width: 6.8 cm. Length/width ratio: 1.39. Shape: Oval. Base: Obtuse. Margin: Doubly serrate.

*Rachis* (*length between terminal leaflet and adjacent lateral leaflets*).—4.4 cm.

*Petiole.*—Length: 8.6 cm. Diameter: 2 mm. Color of upper surface: RHS 139B (Moderate yellowish green). Color of lower surface: RHS 139C (Moderate yellow green).

*Stipule.*—Length: 1 cm. Width: 2 mm. Color: RHS 139C (Moderate yellow green). Orientation: Erect.

Inflorescence:

*Flower bud.*—Length: 8.4 mm. Width: 7.2 mm. Color: RHS 139C (Moderate yellow green).

*Flower.*—Diameter: 40.3 mm. Number of flowers observed at 3$^{rd}$ node from tip of lateral: 10. Fragrance: Very faint or absent.

*Petal.*—Length: 19.1 mm. Width: 12.7 mm. Length/width ratio: 1.50. Number of petals per flower: 5. Color: RHS NN 155C (White). Shape: Oval. Apex: Rounded. Base: Obtuse. Margin: Erose.

*Sepal.*—Length: 10 mm. Width: 4.2 mm. Color: RHS 138D (Light yellow green).

*Flower pedicel.*—Length: 50.4 mm. Diameter: 1 mm. Color: RHS 138C (Moderate yellow green).

*Inflorescence peduncle.*—Length: 34.9 mm. Diameter: 1.7 mm. Color: RHS 138C (Moderate yellow green).

*Reproductive organs.*—Style: Length: 1 mm. Color: RHS 140A (Vivid yellowish green). Ovary: Color: RHS 143B (Strong yellow green). Stamen: Length: 3.9 mm. Color: RHS 145A (Strong yellow green). Pollen: Amount: Medium. Color: RHS 158B (Pale yellow).

*Flowering interval on previous year's cane* (*floricane*).—Early May to June.

Fruit:

*Length of mature fruit.*—30.8 mm.

*Diameter of mature fruit.*—20.4 mm.

*Ratio of length to width.*—1.5.

*Floricane fruit weight.*—10 g/fruit.

*Sweetness/soluble solids* (*in ° Brix*).—13.

*Titratable acidity* (*% as citric acid*).—1.8%.

*Glossiness.*—Medium.

*Firmness.*—Medium.

*Fruit shape in longitudinal section.*—Narrow ovate.

*Fruit color.*—RHS 203A (Black).

*Drupe.*—Length of single drupe: 3.9 mm. Diameter of single drupe: 4.5 mm. Average number of drupes per fruit: 100.

*Seed.*—Diameter: 1 mm. Weight: 0.003 g/seed. Color: RHS 167D (Moderate orange yellow). Abundance: Medium.

*Fruiting on current year's cane.*—Absent.

*Harvest interval on previous year's cane* (*floricane*).—July.

*Yield.*—20,000 lbs to 25,000 lbs of fruit per acre per season from 48-month-old plants when grown in Watsonville, California.

Resistance to pests and diseases:

*Redberry mite* (*Acalitus essigi*).—Moderately susceptible.

*Fusarium wilt* (*Fusarium oxysporum*).—Moderately resistant.

*Verticillium wilt* (*Verticillium* spp.).—Susceptible.

COMPARISON TO PARENTAL AND REFERENCE BLACKBERRY VARIETIES

'DrisBlackThirtyThree' differs from the female parent 'DrisBlackEight' (U.S. Plant Pat. No. 26,501) in that 'DrisBlackThirtyThree' has angular to grooved cross-section of dormant cane, spines absent on dormant cane, absent or very weak undulation of margin on terminal leaflets, and the fruit shape in longitudinal section is narrow ovate, whereas 'DrisBlackEight' has rounded to angular cross-section of dormant cane, spines present on dormant cane, strong undulation of margin on terminal leaflets, and the fruit shape in longitudinal section is long conical. 'DrisBlackThirtyThree' also has higher yield potential and improved plant health compared to 'DrisBlackEight'.

'DrisBlackThirtyThree' differs from the male parent 'DrisBlackTwentyThree' (U.S. Plant Pat. No. 33,067) in that 'DrisBlackThirtyThree' has angular to grooved cross-section of dormant cane, the undulation of margin on terminal leaflet is absent or very weak, the time of beginning of flowering on previous year's cane (floricane) is early, and the fruit shape in longitudinal section is narrow ovate, whereas 'DrisBlackTwentyThree' has rounded to angular cross-section of dormant cane, the undulation of margin on terminal leaflet is weak, the time of beginning of flowering on previous year's cane (floricane) is medium, and the fruit shape in longitudinal section is elliptic. 'DrisBlackThirtyThree' also has firmer fruit, improved plant health, and higher vigor when compared to 'DrisBlackTwentyThree'.

'DrisBlackThirtyThree' differs from the reference variety 'DrisBlackSix' (U.S. Plant Pat. No. 25,502) in that 'DrisBlackThirtyThree' has an upright growth habit, angular to grooved cross-section of dormant cane, the predominant distribution of branches on dormant cane is only on upper third, and absent or very weak undulation of margin on terminal leaflets, whereas 'DrisBlackSix' has a semi-upright growth habit, rounded to angular cross-section of dormant cane, the predominant distribution of branches on dormant cane is over whole length, and weak to medium undulation of margin on terminal leaflets.

'DrisBlackThirtyThree' differs from the reference variety 'DrisBlackThree' (U.S. Plant Pat. No. 23,725) in that 'DrisBlackThirtyThree' has predominant distribution of branches only on the upper third of dormant cane, spines absent on dormant cane, weak blistering between veins on terminal leaflets, and the shape of fruit in longitudinal section is narrow ovate, whereas 'DrisBlackThree' has predominant distribution of branches over the whole length of dormant cane, spines present on dormant cane, medium blistering between veins on terminal leaflets, and the shape of fruit in longitudinal section is oblong.

What is claimed is:

1. A new and distinct variety of blackberry plant designated 'DrisBlackThirtyThree' as shown and described herein.

* * * * *